United States Patent [19]

Jubin

[11] Patent Number: 5,759,795
[45] Date of Patent: Jun. 2, 1998

[54] ASSAY FOR DETERMINING INHIBITORS OF ATPASE

[75] Inventor: Ronald G. Jubin, Watchung, N.J.

[73] Assignee: Schering Corporation, Kenilworth, N.J.

[21] Appl. No.: 612,987

[22] Filed: Mar. 8, 1996

[51] Int. Cl.[6] ........................ C12Q 1/42
[52] U.S. Cl. ................. 435/21; 435/5; 435/8; 435/184
[58] Field of Search ............... 435/21, 5, 8, 69.2, 435/184, 968

[56] References Cited

U.S. PATENT DOCUMENTS

| | | | |
|---|---|---|---|
| 4,264,727 | 4/1981 | Kolehmainen et al. | 435/8 |
| 5,527,669 | 6/1996 | Resnick et al. | 435/5 |
| 5,580,718 | 12/1996 | Resnick et al. | 435/5 |

OTHER PUBLICATIONS

Suzich J., Hepatitis C Virus NS3 Protein Polynucleotide Stimulated Nucleoside Triphosphatase and Comparison with the Related Pestivirus and Flavivirus Enzymes. J. of Virology 67(10) 6152–6158, Oct. 1993.

Yamada E., Calcium Binding ATPase Inhibitor Protein of Bovine Hear Mitochondira, Biochemistry 28 9714–9718, 1989.

*Primary Examiner*—Ralph Gitomer
*Attorney, Agent, or Firm*—Jaye P. McLaughlin; Norman C. Dulak

[57] ABSTRACT

This invention provides materials and methods for identifying inhibitors of a Hepatitis C Virus NS3 protein ATPase. Methods for making and purifying such an ATPase are also provided by this invention.

1 Claim, No Drawings

ASSAY FOR DETERMINING INHIBITORS OF ATPASE

BACKGROUND OF THE INVENTION

Hepatitis C virus (HCV) is considered to be the major etiological agent of non-A non-B (NANB) hepatitis, chronic liver disease, and hepatocellular carcinoma (HCC) around the world. The viral infection accounts for greater than 90% of transfusion -associated hepatitis in U.S. and it is the predominant form of hepatitis in adults over 40 years of age. About a half of the infections result in chronic hepatitis and nearly 20% develop liver cirrhosis.

The virus particle has not been identified due to the lack of an efficient in vitro replication system and the extremely low amount of HCV particles in infected liver tissues or blood. The molecular cloning of the viral genome which has been discovered using the recombinant DNA approach has opened up new avenues of study(B0). It is now known that HCV contains a positive strand RNA genome comprising approximately 9400 nucleotides, whose organization is similar to that of flaviviruses or pestiviruses (B1). The genome of HCV, like that of flavi and pestiviruses, encodes a single large polyprotein of about 3000 amino acids which undergoes proteolysis to form mature viral proteins in infected cells.

Cell-free translation of the viral polyprotein and cell culture expression studies have established that the HCV polyprotein is processed by cellular and viral proteases to produce the putative structural and nonstructural (NS) proteins. At least nine mature viral proteins are produced from the polyprotein by specific proteolysis. The order and nomenclature of the cleavage products are as follows: $NH_2$-C-E1-E2-NS2-NS3-NS4A-NS4B-NS5A-NS5B-COOH. (FIG. 1). The three amino terminal putative structural proteins, C (capsid), E1, and E2 (two envelope glycoproteins), are believed to be produced by host signal peptidases of the endoplasmic reticulum(ER) (B3). The host enzyme is also responsible for generating the amino terminus of NS2 (B4). The proteolytic processing of the non-structural proteins are carried out by the viral proteases: NS2-3 and NS3, contained within the viral polyprotein (B3). The NS2-3 protease catalyzes the cleavage between NS2 and NS3. It is a metalloprotease and requires both NS2 and the protease domain of NS3 (B4). The NS3 protease catalyzes rest of the cleavages in the nonstructural part of the polyprotein. The NS3 protein comprises 631 amino acid residues and contains two enzymatic domains: the protease domain in the amino terminal 181 aa and a ATPase/helicase domain in the rest of the protein (B6). It is not known if the 70 kd NS3 protein is cleaved further in infected cells to separate the protease domain from the helicase domain, however, no cleavage has been observed in cell culture expression studies.

Adenosine triphosphatases (ATPases) are enzymes which catalyze the hydrolysis of Adenosine triphosphate (ATP) releasing energy and one or more inorganic phosphate groups. Many viruses and bacteria including the HCV virus contain a viral or bacterial specific ATPase which is required to catalyze the hydrolysis of an ATP. Potential anti-viral and anti-bacterial agents are substances which would inhibit these ATPases.

Using standard ATPase assays it has been shown that the NS3 sequence encoding amino acids 1193 to 1657 from the H-strain conserved stretches of DNA that are typical of an ATPase and RNA helicase sequence motifs. Using standard ATPase assays with labelled [$\alpha$-$^{32}$P]ATP, it has been demonstrated sequence regions generates the formation of labelled adenosine diphosphate (ADP) presumably by an enzymatic reaction promoted by the truncated NS3 protein [Suzich, J. A. et al. *J. Vir.* 67: 6152–6158 (October 1993)]. Standard ATPase assays are very time consuming and use radioactive isotopes which are a health risk. Thus, there is a need for an efficient high-throughput assay to screen for inhibitors of viral and bacterial ATPases which does not use radioactive isoptopes.

SUMMARY OF THE INVENTION

The present invention fills this need by providing for an assay for screening for inhibitors of an ATPase using luciferase and luciferin. The present invention comprises mixing a test substance with ATP in a buffer containing an ATPase and incubating the mixture. After incubation of the mixture, luciferase and luciferin is added. If light is emitted then the test substance is an ATPase inhibitor because the initial reaction failed to hydrolyze the ATP to ADP and thus ATP is available to drive the the oxidation of luciferon by lucifease. If the substance is not an ATPase inhibitor, then a diminished light signal is seen in the luciferon/luciferase reaction because the ATP was hydrolyzed in the initial reaction. In a preferred embodiment the ATPase is derived from the NS3 non-structural protein of the HCV virus.

DETAILED DESCRIPTION OF THE INVENTION

The present invention is a biochemical assay for screening inhibitors of the hydrolysis of ATP by ATPases. A compound to be analyzed is mixed with an enzyme that has ATP hydrolyzing capabilities and a specific amount of ATP under conditions which, if the test compound does not inhibit ATPase, would result in the hydrolysis of the ATP present. After allowing a sufficient incubation time for the ATPase to perform its activities, the level of ATP remaining in the mixture is determined by a secondary reporter assay using luciferase and its substrate luciferin. In the luciferase/luciferin assay luciferase catalyzes the oxidation of D-luciferin in the presence of ATP-magnesium salt and oxygen wherein the amount of ATP present can be quantified by the amount of light (hv) produced. By comparing the amount of light emitted with the light emitted in a control reaction it is possible to determine the remaining levels of ATP by the light reaction and the molar quantity of available to the luciferase enzyme allowing one to determine the level of ATP hydrolyzed by the ATPase in the initial reaction. The assay can be summarized by the following reaction scheme.

Luciferase Assay Parameters

The Luc/ATPase assay parameters are largely determined by the conditions of the luciferase/luciferin reaction (Reaction 2). The following parameters for the current luc/ATPase assay optimal conditions have been developed using primarily the HCV NS3 N-terminal truncated protein derived from plasmid pQRJDNS3H-8 (Reaction 1). Unless a protein to be analyzed in the system exhibits the same physical reaction conditions as the luciferase/luciferin reaction, the resulting assay format will likely represent some sort of compromise in the light signal generated versus the native enzymatic reaction. Fortunately, the great sensitivity and linear range of the luciferase/luciferin reaction (>8 orders of magnitude) allows one to slightly inhibit reaction 2 without a great compromise in signal to noise ratio of the assay. Variations in the assay buffers and signal analysis can vary greatly upon the protein to be analyzed and the signal recorder. Listed below is a partial list that includes, but should not limit the components of the assay. A simple assay analysis of a new parameters can be easily achieved by running the new conditions and comparing the results to the standard assay conditions of the luciferase/luciferin enzyme reaction (reaction 2).

I. The native firefly luciferase/luciferin reaction:
Components in reaction

1) ATP—Assay linear range measured in a luminometer should be $10^{-16}$M to $10^{-8}$M. (Actual range should be determined experimentally since the sensitivity of different brands of luminometers is known to vary).

2) Luciferin substrate—Assay range of 35 μM to 500 μM The choice of luciferin substrate will depend upon the species of firefly luciferase used. It might be possible to use heterologous enzyme/substrate pairings to achieve optimal light reaction levels or to use artificial benzothiazole substrates capable of enzymatic induced luminescence.(This would have to be determined experimentally).

3) Luciferase enzyme—Assay range of $10^{-20}$M to 1 μM. Firefly luciferases generate the greatest the greatest light signal of all bioluminescent proteins cloned and expressed to date. The Luc/ATPase assay takes advantage of this situation by using the luciferase enzyme from the common American firefly (Photinus pyralis). It should not however be limited to this enzyme only. Rather it should include all firefly luciferases. But assay enzymes should not limited by species. but rather by a requirement for ATP in the reaction. Recent phylogenetic studies have grouped ANgR form a pathogenic bacterium and acetyl-CoA synthetases from two ascomyte fungi as sharing several characteristics with firefly luciferases.

5) Magnesium$^{2+}$—Assay range of 1 to 12 mM concentration. However the list should not be limited to $Mg^{2+}$ as other divalent cations including $Mn^{2+}$, $Zn^{2+}$, $Co^{2+}$, $Ni^{2+}$, $Cd^{2+}$ or $Ca^{2+}$ can be substituted with limited compromise to the assay signal.

6) Luminescence Recorder—Although the recorder just monitors the assay activity, the sensitivity of the system will likely play an important role in assay components (e.g. luminometers vs. scintillation counters)

BUFFER CONSTITUENTS (not listed in the general enzymatic equation above)

In addition to the buffer components listed in the materials section. certain additions to assay components can act to stabilize or enhance the enzymatic activities of Reaction 2. Listed below is a partial list of assay buffer component additions that either enhance. stabilize or have no detrimental effects (but help out in Reaction 1) on the luciferase/luciferin reaction.

Buffers
  Tris-HCl buffers (ph 7.2, 7.5 and 8.0)
  Sodium phosphate buffers
  Tricine buffers
  Glycylglycine
  HEPES
Stabilizers/detergents
  EDTA (limiting amounts <20 mM)
  B-mercaptoethanol
  DTT
  Coenzyme A
  Bovine Serum Albumin
  Triton X-100
  Glycerol
  DMSO (<0.2%)

NOTE: An entire different set of parameters could also be achieved by dilution of reaction 1 into reaction 2 to acceptable levels of light generating activity.

LUC/ATP ASSAY

MATERIALS AND METHODS: The following lists the components used in the assay. While the current optimal concentrations are listed, these are subject to change depending upon the experimental conditions.

1. Materials
  a. Buffer A (sample buffer that refolded enzymes are stored in.)
    25 mM N-2-hydroxyethylpiperazine-N'-2-ethanesulfonic acid [HEPES]
    1 mM ethylenediaminetetriacetic acid [EDTA]
    50 mM Potassium chloride
    0.02% 2-mercaptoethanol
    0.01% Triton X-100
    50% Glycerol
  b. Luc/ATP Buffer (assay buffer)
    10 mM Tris-HCl (pH7.2)
    30 mM NaCl
    5 mM 2-mercaptoethanol
    45 uM adenosine triphosphate (ATP)
    2.5 mM Magnesium chloride
    25 mM Glycylglycine
  c. Dilution Buffer (for diluting enzyme samples to equal volumes)
  Same as b.—without the addition of ATP
  d. Luciferase enzyme from photinus pyralis (American firefly)
  A 1 mg/ml concentrated stock solution is prepared in 0.5 mol/L tris acetate buffer (pH 7.5).
  Concentrated stock is diluted to 1 mg/ml in Dilution buffer.
  e. Luciferin substrate D(-)-Luciferin from Photinus pyralis
  Powdered stock is diluted into sterile water with a final concentration of 0.3 mg/ml. Depending upon assay conditions, between 90 and 100 ul of substrate is added per reaction well.
  f. Micro-plates (96-well) designed for use in luciferase reactions.
  g. Luminometer for recording the light reaction signal.

2. Methods

The methodology behind the assay is a two-step coupled process where an enzyme that possesses ATP hydrolyzing capabilities is mixed in assay buffer containing ATP [Reaction 1] (buffers will vary depending upon the individual properties of the enzyme to be tested e.g. salt conc., pH, etc.). After allowing a sufficient incubation time for the enzyme to perform its' activities the level of ATP remaining in the reaction mix is monitored by the secondary (reporter) assay [Reaction 2]. This luciferase/luciferin reaction is dependent upon a variety of factors (see flowchart) including ATP. it is possible to quantitate the levels of ATP in the reaction mix by monitoring the light excitation signal generated by the reaction. By comparing values with control values (ATP titration of the luciferase/luciferin reaction independently) it will be possible to determine the remaining levels of ATP by the light reaction and the molar quantity available to the luciferase enzyme allowing you to determine the level of ATP hydrolyzed in reaction 1.

a. Procedure for analyzing NS3 ATPase activity

An enzyme sample prep (in Buffer A) is mixed with Assay buffer (dilution buffer is used to standardize volumes of different enzyme preps if necessary).

After allowing incubation for a time period. luciferase enzyme is added to all the samples.

Immediately following the addition of luciferase. the plate is loaded into the luminometer and luciferin substrate is added to an individual well and the light reaction is recorded as Relative Light Units (RLU's). This process is repeated in a well to well stepwise fashion for the entire plate.

LUC/ATP ASSAY

MATERIALS AND METHODS: The following lists the components used in the assay. While the current optimal concentrations are listed, these are subject to change depending upon the experimental conditions.

1. MATERIALS

I. Protein expression/purification a. EXPRESSION

M15 *E. coli* [qiagen]

20-10-5 Broth

Isopropyl-b-D-thiogalactoside (IPTG) [BoehringerMannheim]

Erlenmeyer flasks

Incubator (37° C.) with shake platform (285 rpm)

b. PURIFICATION

GLUCOSE/EDTA/TRIS BUFFER 50 mM glucose [Sigma]

10 mM ethylenedinitrilo tetraacetic acid disodium salt (EDTA) [Gibco BRI]

25 mM Tris-HCl ph8.0 [Gibco BRI]

250 ug/ml lysozyme [BoehringerMannheim]

additions

1% Triton X-100 [BoehringerMannheim]

20 mM Magnesium Chloride [Fisher Biotech]

200U DNAse 1 [BoehringerMannheim]

SUCROSE/STE CUSHION

35% Sucrose [BoehringerMannheim]

150 mM sodium chloride [Sigma]

10 mM tris-Hcl ph7.4 [Gibco BRI]

1 mM EDTA [Gibco BRI]

RESUSPENSION BUFFER 1

10 mM glycine-NaOH ph10.5 [BoehringerMannheim]

1% Triton X-100 [BoehringerMannheim]

2 mM EDTA [Gibco BRI]

SOLUBILIZATION BUFFER 5M guanidine-HCl [BoehringerMannheim]

50 mM Tris-HCl ph8.0 [Gibco BRI]

1 mM EDTA [BoehringerMannheim]

DIALYSIS BUFFER 1

0.5M guanidine-HCl [BoehringerMannheim]

50 mM Tris-HCl ph8.0 [Gibco BRI]

1 mM EDTA [BoehringerMannheim]

1 mM EDTA [Gibco BRI]

1 mM 1,4-Dithiothreithol (DTT) [BoehringerMannheim]

20% Glycerol [Fisher Biotech]

BUFFER A 25 mM N-2-hydroxyethylpiperazine-N'-2-ethanesulfonic acid(HEPES) ph7.4 [JRH Biosciences]

50 mM potassium chloride [Sigma]

1 mM EDTA [Gibco BRI]

0.02% b-mercaptoethanol [Sigma]

0.01% Triton X-100 [BoehringerMannheim]

50% glycerol [Fisher Biotech]

II. Luc/ATPase assay a. HCV NS3 ATPase ACTIVITY

ASSAY BUFFER (AB+)

10 mM Tris-HCl (ph7.2)

30 mM NaCl 5 mM 2-mercaptoethanol

45 µM adenosine triphosphate (ATP)

2.5 mM Magnesium chloride 25 mM Glycylglycine

DILUTION BUFFER (AB−) (for diluting luciferase resuspension of luciferin and diluting samples to equal volumes)

Same as AB+ without the addition of ATP b. LUCIFERASE REACTION

LUCIFERASE ENZYME from *Photinus pyralis* (American firefly) [BoehringerMannheim]

A 1 mg/ml concentrated stock solution is prepared in 0.5 mol/L tris acetate buffer (pH 7.5).

Concentrated stock is diluted to 1 µg/ml in Dilution buffer at time of assay.

LUCIFERIN SUBSTRATE D(−)-Luciferin from *Photinus pyralis* [BoehringerMannheim]

Powdered stock is diluted into sterile AB− with a final concentration of 0.3 mg/ml. Depending upon assay conditions, between 90 and 100 ul of substrate is added per reaction well.

Micro-plates (96-well) designed for use in luciferase reactions.[Dynatech]

Luminometer for recording the light reaction signal. [Dynatech laboratories][Model ML3000 Microtiter plate luminometer]

2. METHODS

I. Protein expression/purification a. CONSTRUCTION

The HCV ATPase gene and protein (SEQ ID NO: 3) were produced as follows. The The plasmid pBRTM/HCV 1-3011 containing the entire HCV genome (Grakoui, A., et al., *J. Virol.* 67: 1385–1395) was digested with the restriction enzymes Sca1 and Hpa1 and the 7138 base pair (bp) fragment was isolated and cloned into the Sma1 site of pSP72 (Promega) to produce plasmid pRJ201. The plasmid pRJ201 was digested with Msc1 and the 2106 bp fragment was isolated and cloned into the Sma1 site of pBD7 (Dasmahapatra, et al *Nucl. Ac. Res.* 15: 3933). The resulting plasmid pMBM48 was digested with Kas1 and Nco1 followed by treatment with Klenow polymerase the 734 bp fragment was isolated and cloned into Nco1 digested, Klenow polymerase treated pTrcHIS B seq expression plasmid (Invitrogen). The ligation regenerated a Nco1 site at the 5' end and an Nsi1 site at the 3' end of the HCV sequence. The plasmid pTHB HCV NS3 was then digested with Nco1 and Nsi1 and treated with klenow polymerase and T4 DNA polymerase to produce a blunt ended 738 bp DNA fragment. This fragment was isolated and cloned into Asp1 cut, Klenow polymerase treated expression plasmid pQE30 (HIV). The resulting plasmid BJ1015 expresses the HCV NS3 246 amino acid (aa) HCV NS3 proteinase. Plasmid pTS56-9 was constructed to place a stop codon after amino acid 183. The plasmid pTHB HCV NS3 was digested with Nco1, treated with Klenow polymerase, then digested with BstY1 and the DNA fragment containing HCV sequence was isolated and cloned into Sma1 and Bgl2 digested pSP72. The resulting plasmid pTS49-27 was then digested with Bgl2 and Hpa1 and ligated to the double stranded oligonucleotide:

to produce pTS56-9. Thus a stop codon was placed directly at the end of DNA encoding the proteinase catalytic domain of the NS3 protein.

Full length HCV NS3 clone were prepared by digesting pRJ201 with Bgl2 and BamH1 generating a 4293 bp fragment that was cloned into pBD7, BamH1 digested. Plasmid pRJ202 was digested with Kas1 followed by treatment with Klenow polymerase. The 2428 bp fragment encoding for the entire NS3, NS4A and the N-terminal 125aa of NS4B was isolated and ligated into JFR123 (in house) creating an ompA/HCV fusion protein. Plasmid pONS3-13 was created by digesting pRJ206 with Eag1 and BamH1 then ligated to the double stranded oligonucleotide:

This created a stop at the C-terminal of the HCV NS3 protein at the identical site of polyprotein processing as indicated in the literature (Grakoui, A., et al., J. Virol. 67: 1385–1395). A full length fusion protein was also created by fusing the isolated NgoM1, BamH1/klenow polymerase fragment of pONS3-13 into the NgoM1, Sal1/klenow digested pBJ1015.

(A) Plasmid pRJ183-2 was constructed by cloning the Nco1/Bgl2 NS3 containing fragment from pTS56-9 into the identical sites of pQE-60 expression vector (Qiagen). This plasmid encoded for E. coli expression of the NS3 proteinase domain under control of the IPTG inducible E. coli T5 phage promoter.

(B) Plasmid pRJ631-3 was constructed by digesting pT5HIS/HIV631-3 with BstX1 and Hind3 and isolating the NS3 C-terminal 1435 bp fragment and ligating it into pRJ183-2 digested with BstX1 and Hind3. This generates a full-length native NS3 expression construct.

(C) Plasmid pQRJDNS3H-8 was constructed by digesting pONS3-13 with BstX1 and BamH1 followed by treatment with T4 DNA poymerase. This fragment was ligated into pQE-70 digested with Nco[1 ]followed by Klenow polymerase treatment. The resulting plasmid contains the putative NTPase/helicase domains of HCV NS3.

b. EXPRESSION

Plasmids pRJ631-3, pQRJDNS3H-8 and pRJ183-2 were transformed individually into E. coli strain M15 (Qiagen) by standard heatshock methods. Clones expressing the recombinant proteins were determined by 1) antibiotic selection (ampicillin and kanamycin;100 ug/ml and 25 ug/ml, respectively), 2) restriction analysis of the recombinant DNA plasmid, 3) Small scale expression in 20-10-5 broth containing selective antibiotics with subsequent analysis of cell lysates by SDS-PAGE separation coomassie, 4) SDS-PAGE gels were either stained with coomassie blue or transferred to polyvinylidene difluoride (PVDF) membranes by electrophoresis (western blot). Western blot samples were probed with anti-NS3 444 antibody followed by anti-Rabbit-alkaline phosphatase antibody. Clones meeting all of the above criteria were selected for purification/activity studies.

50 ml culture expression samples were grown for purification purposes as follows: 3 ml overnight cultures are inoculated from glycerol stocks and grown o/n 37° C./285 rpm. Following determination of the Optical density (OD) value of the culture at 6001, the culture is diluted onto fresh media to achieve a starting OD600=0.2. The culture(s) is allowed to grow at 37° C./285 rpm until an O.D.600 value of 0.8 is achieved. At this point, IPTG (0.5 mM) is added to the culture vessels to induce heterologous protein expression. Cultures are harvested at 4 hours post-induction by centrifugation. The E. coli pellets are either frozen at −80° C. or processed immediately as outlined below.

c. PURIFICATION

1a) E. coli pellets are resuspend in 4 ml GLUCOSE/EDTA/TRIS buffer.
Incubate for 20 minutes at 4° C.

2a) Cultures were adjusted to 1% Triton X-100—sonicate extensively.

2b) MgCl2 (20 mM) and DNase I (10 μg/ml) were added to cultures.
Incubate an additional 20 min. at 24° C.

3) E. coli suspensions were then layered onto a 0.75 ml SUCROSE/STE cushion.
Centrifuge 30 minutes at 30,000×g (4° C.).

4) Pellets were resuspended in 2 ml RESUSPENSION BUFFER 1.
Incubate for 60 minutes at 4° C. Centrifuge 10 minutes at 10,000×g.

5) Resuspend pellets in 2 ml SOLUBILIZATION BUFFER by brief sonication.
Incubate 60 minutes at 4° C. spin 20 minutes at 20,000×g.

6) Collect supernatant and Dialyze overnight (at 4° C.) against 500 volumes of DIALYSIS BUFFER 1.

7) Dialysates cleared and dialyzed against 500 VOLUMES Buffer A.

8) Post-dialysis samples were transferred to 1.5 ml polypropylene tubes (Eppendorf) and stored at −20° C.

NOTE: Samples are first confirmed for expression level by SDS-PAGE analysis as outlined in the Methods section (part b—expression).

II. Luc/ATPase assay a. TEST MOLECULE DILUTION

Samples that are supplied at 1 mg/ml conc (100% DMSO) are diluted into AB− to a concentration of 2 μg/ml (0.2%DMSO).

NOTE: Sample prep will vary with the initial concentration and source of test materials.

b. ASSAY FOR INHIBITORS

The methodology behind the assay is a two-step coupled process where an enzyme that possesses ATP hydrolyzing capabilities is mixed in assay buffer containing ATP [Reaction 1] (buffers will vary depending upon the individual properties of the enzyme to be tested e.g. salt conc., pH, etc.). After allowing a sufficient incubation time for the enzyme to perform its' activities, the level of ATP remaining in the reaction mix is monitored by the secondary (reporter) assay [Reaction 2]. This luciferase/luciferin reaction is dependent upon a variety of factors including ATP levels. It is therefore possible to quantitate the levels of ATP hydrolyzed in reaction 1 mix by monitoring the light excitation signal generated by reaction 2. By comparing test values with control values (ATP titration of the luciferase/luciferin reaction independently) it will be possible to determine and quantify the inhibition of ATP hydrolysis that had occurred in reaction 1.

REACTION 1

1) Microtiter assay plates are filled with 85 ul AB+ containing ATP.

2) Drug dilution samples are added to a final volume of 10 ul/well (typically 2 μg/ml conc.).

3) 10 μl of pQRJDNS3H-8 or pRJ631-3 (or pRJ183-2 as a negative control) are added per well.
(if dilution is necessary it is performed with buffer A)

4) allowed to occur by incubating plates for 2 hours at room temperature.

REACTION 2

5) 10 μl per well of luciferase enzyme is added per well (10 ng).

6) 90 ul of luciferin substrate is added per well (18 μg).

7) samples are assayed in the luminometer for Relative light units produced by the Luciferase/Luciferin reaction.

NOTE: While the assay is directed towards the discovery of inhibitors, it can likewise be adapted to analyze activators that increase ATPase activity of the HCV NS3 enzyme.

What is claimed is:

1. A method for identifying an inhibitor of a Hepatitis C Virus NS3 protein ATPase comprising:

(a) incubating a reaction mixture comprising Hepatitis C Virus NS3 protein ATPase enzyme in the presence of (i)

a sample suspected to contain an inhibitor of such enzyme and (ii) a specific amount of ATP, under conditions in which the enzyme in the absence of such inhibitor hydrolyzes ATP to form ADP;

(b) subjecting the reaction mixture from step (a) to a luciferase reaction, under conditions in which ATP remaining in the reaction mixture produces light emission; and (c) measuring the light emitted in step (b), whereby an inhibitor of the Hepatitis C Virus NS3 protein ATPase in the sample is identified by measurement of a substantially greater amount of light than would be measured in the presence of a control sample lacking such inhibitor.

* * * * *